United States Patent
Ho et al.

(10) Patent No.: US 10,426,642 B2
(45) Date of Patent: Oct. 1, 2019

(54) MEMBRANE FOR COVERING A PERIPHERAL SURFACE OF A STENT

(71) Applicants: National University of Singapore, Singapore (SG); Agency for Science, Technology and Research, Singapore (SG)

(72) Inventors: Pei Ho, Singapore (SG); Hwa Liang Leo, Singapore (SG); Sum Huan Ng, Singapore (SG); Fangsen Cui, Singapore (SG); Foad Kabinejadian, Singapore (SG)

(73) Assignees: National University of Singapore, Singapore (SG); Agency for Science, Technology and Research, Singapore (SG)

(*) Notice: Subject to any disclaimer, the term of this patent is extended or adjusted under 35 U.S.C. 154(b) by 685 days.

(21) Appl. No.: 14/350,690

(22) PCT Filed: Oct. 9, 2012

(86) PCT No.: PCT/SG2012/000377
§ 371 (c)(1),
(2) Date: Apr. 9, 2014

(87) PCT Pub. No.: WO2013/055293
PCT Pub. Date: Apr. 18, 2013

(65) Prior Publication Data
US 2014/0358221 A1    Dec. 4, 2014

(30) Foreign Application Priority Data

Oct. 10, 2011 (SG) .............................. 201107555-3

(51) Int. Cl.
*A61F 2/856* (2013.01)
*A61F 2/915* (2013.01)
(Continued)

(52) U.S. Cl.
CPC .............. *A61F 2/856* (2013.01); *A61F 2/915* (2013.01); *A61F 2/07* (2013.01); *A61F 2/24* (2013.01);
(Continued)

(58) Field of Classification Search
CPC .................................. A61F 2/82; A61F 2/856
See application file for complete search history.

(56) References Cited

U.S. PATENT DOCUMENTS 5,575,818 A * 11/1996 Pinchuk .................... A61F 2/90
606/195
6,334,868 B1   1/2002 Ham
(Continued)

FOREIGN PATENT DOCUMENTS

| CN | 101627933 | 1/2010 |
| EP | 1923025 | 5/2008 |

(Continued)

*Primary Examiner* — Matthew W Schall
(74) *Attorney, Agent, or Firm* — K. David Crockett, Esq.; Niky Economy Syrengelas, Esq.; Crockett & Crockett, PC

(57) ABSTRACT

A membrane for covering a peripheral surface of a stent is provided, the membrane including a plurality of line openings formed therein. Each line opening may be a straight line opening, for example in the form of a slit, a curved line opening, or any line opening of a suitable shape or curvature, e.g. U-shaped or V-shaped. Blood pressure opens the slits to allow blood to flow through the membrane, while curved line openings create a flap in the membrane that can open to allow blood to pass through. According to further embodiments of the present invention, a method of forming a membrane on a stent and a device for use in a blood vessel are provided.

15 Claims, 10 Drawing Sheets

(51) Int. Cl.
*A61F 2/07* (2013.01)
*A61F 2/24* (2006.01)

(52) U.S. Cl.
CPC ............... *A61F 2002/072* (2013.01); *A61F 2002/91575* (2013.01); *A61F 2220/005* (2013.01); *A61F 2220/0075* (2013.01); *A61F 2240/001* (2013.01); *A61F 2250/0071* (2013.01)

(56) References Cited

U.S. PATENT DOCUMENTS

| | | | |
|---|---|---|---|
| 8,088,157 B2 | 1/2012 | Fierens et al. | |
| 2001/0032009 A1 | 10/2001 | Layne et al. | |
| 2003/0023303 A1 | 1/2003 | Palmaz et al. | |
| 2005/0131515 A1* | 6/2005 | Cully | A61F 2/07 623/1.13 |
| 2005/0186241 A1* | 8/2005 | Boyle | A61B 5/076 424/423 |
| 2006/0142845 A1 | 6/2006 | Molaei et al. | |
| 2006/0259132 A1 | 11/2006 | Schaffer et al. | |
| 2008/0114446 A1 | 5/2008 | Hartley et al. | |
| 2012/0323309 A1 | 12/2012 | Cattaneo | |
| 2014/0249620 A1* | 9/2014 | Carman | A61F 2/07 623/1.39 |

FOREIGN PATENT DOCUMENTS

| | | |
|---|---|---|
| WO | WO9853759 | 12/1998 |
| WO | WO2008057568 | 5/2008 |
| WO | WO2009055723 | 4/2009 |
| WO | WO2011076408 | 6/2011 |

* cited by examiner

MEMBRANE FOR COVERING A PERIPHERAL SURFACE OF A STENT

CROSS-REFERENCE TO RELATED APPLICATION

This application claims the benefit of priority of Singapore patent application No. 201107555-3, filed 10 Oct. 2011, the content of it being hereby incorporated by reference in its entirety for all purposes.

TECHNICAL FIELD

Various embodiments relate to a membrane for covering a peripheral surface of a stent, and a method of forming a membrane on a stent. Further embodiments relate to a device for use in a blood vessel and use of the device for treating disease of a blood vessel that may cause release of emboli into the distal circulation, while allowing perfusion of blood into a side branch of the blood vessel. Further embodiments relate to a stent including a plurality of line openings formed therein.

BACKGROUND

Stenosed carotid artery results in stroke which is one of the leading causes of death, disability and hospital admission. There is, recently, an increasing interest in carotid artery stenting (CAS) for treatment of cervical carotid artery bifurcation atherosclerotic disease.

Unlike atherosclerotic disease in other vascular locations (e.g. the coronary and lower limb arteries), the main concern regarding CAS is atherothrombotic emboli going into intracerebral circulation, rather than hemodynamic insufficiency, which means that carotid stenosis causes stroke not by reducing blood flow rate but by releasing emboli into the distal circulation. However, the current stents used for CAS are modified from stents used to treat obstructive arterial disease of the coronary or peripheral arteries, which do not address the emboli issue.

Conventional carotid artery stenting (CAS) reduce emboli release from the diseased carotid artery by forming a scaffold over the atherosclerotic plaque. However, the effectiveness of the metal struts of the bare metal stent to confine all loose fragments of the atherosclerotic plaque is unreliable. Modification of the stent design or reducing the cell size of a stent maximally may prevent large size emboli from being released from the atherosclerotic plaque but would not be effective for small to moderate size emboli. The size of plaques released during CAS ranged from 3.6 µm to >5000 µm, which are mostly smaller than the size of a cell in a carotid stent.

Embolic protection device was developed to trap any loose fragments going into the distal circulation during the stenting procedure. Its protection is only available during the procedure. It has been observed that about 40% of the CAS stroke events happen between 7 and 30 days after the stenting procedure. Thus, emboli protection during the procedure only is not sufficient to prevent procedure related stroke. Furthermore, there is no significant reduction of the number of micro-emboli detected by brain magnetic resonance imaging (MRI) for CAS patients with or without embolic protection devices. The current bare metal stents and emboli protection devices cannot fully address the fundamental problem of various sizes of emboli released during and after carotid artery stenting for an unstable atherosclerotic plaque.

The use of covered carotid stents, while offering better protection against emboli to the cerebral circulation, cannot be a proper solution as carotid bifurcation is involved in most cases, as the covered carotid stents will unavoidably jeopardize the perfusion of blood into the external carotid artery (ECA). This may affect the hemodynamics over the carotid bifurcation and might also affect cerebral circulation as it is not uncommon for external carotid artery to develop collaterals into the brain in chronic disease condition.

Accordingly, much effort has been put and some different designs of covered and membrane carotid stents have been suggested, in order to achieve emboli prevention and at the same time maintain the ECA branch blood flow. However, none of them is devoid of complications.

Atherosclerotic disease causing emboli to the distal circulation also happened in aorta. Currently, covered stent namely stent-graft can be used to control the emboli going into circulation. However, if the diseased part of the aorta is close to an important branch, the treatment will become more difficult and may involve additional surgical bypass procedure.

SUMMARY

According to an embodiment, a membrane for covering a peripheral surface of a stent is provided. The membrane may include a plurality of line openings formed therein.

According to an embodiment, a method of forming a membrane on a stent is provided. The method may include forming the membrane on a peripheral surface of the stent, and forming a plurality of line openings in the membrane.

According to an embodiment, a device for use in a blood vessel is provided. The device may include a stent configured to be received in the blood vessel, and a membrane configured to cover a peripheral surface of the stent, wherein the membrane includes a plurality of line openings formed therein.

According to an embodiment, use of the device as described above for treating a blood vessel disease which may cause emboli to be released into the distal circulation and at the same time preserving perfusion of blood into a side branch of the blood vessel, is provided.

According to an embodiment, a stent including a plurality of line openings formed therein is provided.

BRIEF DESCRIPTION OF THE DRAWINGS

In the drawings, like reference characters generally refer to the like parts throughout the different views. The drawings are not necessarily to scale, emphasis instead generally being placed upon illustrating the principles of the invention. In the following description, various embodiments of the invention are described with reference to the following drawings, in which.

DETAILED DESCRIPTION

Figure 1A:
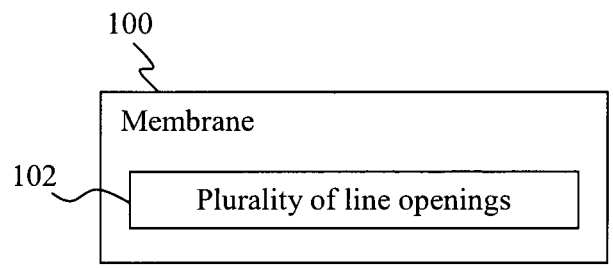
FIG. 1A shows a schematic block diagram of a membrane for covering a peripheral surface of a stent, according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural and logical changes may be made without departing from the scope of the invention. The various embodiments are not necessarily mutually exclusive, as some embodiments can be combined with one or more other embodiments to form new embodiments.

Embodiments described in the context of one of the devices are analogously valid for the other device. Similarly, embodiments described in the context of a method are analogously valid for a device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the phrase "at least substantially" may include "exactly" and a reasonable variance.

As used herein, the term "and/or" includes any and all combinations of one or more of the associated listed items.

Various embodiments may relate to the field of endovascular surgery. Various embodiments may relate to endovascular treatments of atherosclerotic and degenerative lesion in the blood vessel and for example where perfusion of blood to a side branch of a diseased vessel needs to be preserved. Various embodiments may be suitable for patients with carotid artery stenosis and may provide for carotid artery stenting for treatment of carotid artery stenosis. The approach of various embodiments may work in complement with existing technologies to reduce the embolic events related to carotid artery stenting (CAS). Various embodiments may be suitable for patients with aortic mural thrombus for preventing or minimising emboli going into the blood circulation.

Various embodiments of the membrane and the device (e.g. a carotid stent) including the membrane may be suitable to minimise or prevent friable fragments of a diseased blood vessel (e.g. emboli from an atherosclerotic plaque) from getting into the circulation while at the same time preserving the flow of blood into a side branch of a blood vessel (e.g. the external carotid artery (ECA)).

Various embodiments may provide a stent with a peripheral surface which is covered or coated with a thin layer of biocompatible membrane with a plurality of line openings made or formed in the membrane. The membrane may be either biodegradable or non-biodegradable. For example, the membrane may degrade over time, such as over a period of time after the stenting procedure. The membrane should however last for example at least until the atherosclerotic plaque is stabilized. The membrane may be made of polymers, biological materials or thin layer of metals. In various embodiments, the membrane and the stent may also be carved out or formed from a single tube, e.g. a metal tube, a tube of a synthetic material, e.g. a polymeric tube.

Various embodiments may provide a preferential covered stent for embolic prevention and preservation of side branch perfusion. Various embodiments may provide a membrane for covering a peripheral surface of a stent. Various embodiments may provide a membrane having a plurality of flaps, where each flap is partially bounded by a line opening formed in the membrane, and a stent (e.g. a carotid stent) covered on its peripheral surface with such a membrane. Various embodiments may also provide a membrane having a plurality of slits, e.g. of a straight linear form, formed in the membrane, and a stent (e.g. a carotid stent) covered on its peripheral surface with such a membrane. Therefore, various embodiments may provide a membrane having a plurality of line openings formed therein. Each line opening may be shaped to define a partial boundary of a flap, or each line opening may define a slit.

Various embodiments may provide a stent with its peripheral surface covered or coated with a membrane, wherein multiple line openings in the form of slits are created in the membrane. The slits may be configured in such a way that blood flowing through the stent placed into a blood vessel may open the slits located in an area of the membrane facing a side branch of the blood vessel. For example the slits may expand outwardly from the membrane to define respective pores or openings, and allow perfusion of blood into the side branch of the blood vessel. In a non-branched area of the blood vessel (i.e. an area without a side branch), the membrane may be pushed against the blood vessel wall so that the slits remain in a closed configuration. Therefore, the membrane and the closed slits may act as a barrier between the blood vessel inner wall (with possible associated plaques) and the blood flow inside the lumen of the blood vessel.

Various embodiments may provide a stent with its peripheral surface covered or coated with a membrane in which multiple flaps are created in the membrane, where each flap is partially bounded by a line opening. The flaps may be configured in such a way that blood flowing through the stent placed into a blood vessel may open, at least partially, the flaps located in an area of the membrane facing a side branch of the blood vessel. For example the flaps may extend outwardly from the membrane, and allow perfusion of blood into the side branch of the blood vessel. In a non-branched area of the blood vessel (i.e. an area without a side branch), the membrane may be pushed against the blood vessel wall so that the flaps remain in a closed configuration. Therefore, the membrane and the closed flaps may act as a barrier between the blood vessel inner wall (with possible associated plaques) and the blood flow inside the lumen of the blood vessel.

In various embodiments, a device including a bare stent (e.g. a bare metal stent) covered with a biocompatible polymer membrane, for example including but not limited to polyurethanes and polycarbonate urethanes (e.g. Chronoflex AR), may be provided. Line openings may be created in the polymer membrane in stent cells defined by struts of the stent. The line openings may be, for example in the form of slits, or may define respective partial boundaries of flaps, which may open to create openings in the membrane. The flaps or slits may therefore allow blood flow through the stent polymer membrane into openings and branches (e.g. ECA) of the blood vessel, where the polymer membrane also secures the plaques at blood vessel wall locations and prevent any loose fragments (e.g. emboli from an atherosclerotic plaque) from dislodging and entering the blood circulation. Accordingly, various embodiments enable preferential blood flow to a side branch of a blood vessel in the presence of a covered stent in the blood vessel.

It should be appreciated that the membrane of various embodiments may include a plurality of flaps and a plurality of slits.

FIG. 1A shows a schematic block diagram of a membrane 100 for covering a peripheral surface of a stent, according to various embodiments. The membrane 100 includes a plurality of line openings 102 formed therein.

In the context of various embodiments, the term "peripheral surface" with regard to a stent may mean an inner peripheral surface or an outer peripheral surface of the stent so that the membrane may cover the inner or the outer peripheral surface of the stent. In other various embodiments, the "peripheral surface" with regard to a stent may mean both the inner and the outer peripheral surfaces so that the membrane is formed on both the inner and the outer peripheral surfaces of the stent as a single membrane, e.g. by embedding the stent into the membrane. More generally, the "peripheral surface" with regard to the stent may refer to the peripherally open surfaces of the stent formed by cells of the stent defined and bordered by struts of the stent. In any case, the membrane may be arranged on the peripheral surface of the stent so as to provide a stent-membrane structure which is, apart from the line openings, closed at its periphery. In the context of various embodiments, the distance between the inner peripheral surface and the outer peripheral surface of a stent defines a thickness of the stent.

In the context of various embodiments, each line opening 102 may be a straight line opening, for example in the form of a slit, a curved line opening, or any line opening of a suitable shape or curvature, e.g. U-shaped or V-shaped.

In the context of various embodiments, the plurality of line openings 102 may be formed at a portion or an area of the membrane 100 or throughout the membrane 100.

In the context of various embodiments, the plurality of line openings 102 may be oriented in a same direction or in different directions, for example parallel to or perpendicular to or at an angle to an axis of the membrane 100, for example, a transverse axis or a longitudinal axis of the membrane 100.

In various embodiments, each line opening 102 may be a straight line opening, for example a slit. The slit may allow a fluid, e.g. blood, to pass through, when the slit is in an open position. As a non-limiting example, as the blood flows through the membrane 100, the pressure gradient of the blood flow may expand slits that are positioned at a side branch of a blood vessel and not against a blood vessel wall, so as to define respective pores or apertures or openings in an open position, through which the blood may flow through; for example, to the side branch of the blood vessel. Where the membrane 100 is positioned against a blood vessel wall, the slits are pushed against the wall and unable to expand, and are therefore in a closed position.

In various embodiments, the slits may have a length of between about 300 µm (0.3 mm) and about 1500 µm (1.5 mm), for example between about 300 µm and about 1000 µm, between about 300 µm and about 700 µm, between about 500 µm and about 1000 µm or between about 500 µm and about 700 µm, e.g. about 300 µm, about 500 µm, about 700 µm or about 1000 µm.

In various embodiments, the number of slits formed may depend on the dimensions (e.g. length and diameter) of the membrane 100. In addition, the density of the slits may be variable.

In various embodiments, each line opening 102 of the plurality of line openings 102 may be shaped to define a partial boundary of a portion of the membrane 100 therewithin, wherein the portion defines a flap. Therefore, the membrane 100 may include a plurality of flaps formed therein, each flap corresponding to a line opening 102 that defines a partial boundary of the flap. The plurality of flaps may be formed from part of the membrane 100. In various embodiments, each line opening 102 may be shaped in the form of a curved line opening, for example U-shaped. In various embodiments, the plurality of flaps may be defined or formed at a portion or an area of the membrane 100 or throughout the membrane 100.

In the context of various embodiments, each flap may be pivotable between an open position in which the flap extends outwardly from the membrane 100 thereby defining an opening in the membrane 100, and a closed position in which the flap extends in line with the membrane 100 thereby at least substantially closing said opening. Therefore, the membrane, when used for covering a peripheral surface of a stent (e.g. a bare-metal stent), may provide a preferential covered stent, e.g. allowing perfusion of blood through the flaps into a side branch area of a blood vessel, while preventing blood flow through the flaps in a non-branched area of a blood vessel, thereby preventing plaque fragments from getting into the blood circulation.

In the context of various embodiments, each flap may be formed in the membrane 100 with a connecting section of the membrane 100 extending between two ends of the line opening 102.

In the context of various embodiments, the plurality of flaps may have any dimensions, depending on requirements such as the size of the flaps, arrangement of the flaps, density of the flaps, distance between adjacent flaps, and thickness of the membrane 100.

In the context of various embodiments, the length of the connecting section of each flap between the two ends of the line opening 102 defining the partial boundary of the flap (illustrated as dimension m in FIGS. 4D to 4F), may be between about 300 µm (0.3 mm) and about 1500 µm (1.5 mm), for example between about 300 µm and about 1000 µm, between about 300 µm and about 700 µm, between about 500 µm and about 1000 µm or between about 500 µm and about 700 µm, e.g. about 300 µm, about 500 µm, about 700 µm or about 1000 µm.

In the context of various embodiments, the distance between the connecting section of each flap and the tip or the furthest point of the flap, along a line perpendicular to the connecting section (illustrated as dimension n in FIGS. 4D to 4F), may be between about 300 µm (0.3 mm) and about 1500 µm (1.5 mm), for example between about 300 µm and about 1000 µm, between about 300 µm and about 700 µm, between about 500 µm and about 1000 µm or between about 500 µm and about 700 µm, e.g. about 300 µm, about 500 µm, about 700 µm or about 1000 µm.

In the context of various embodiments, the thickness of the membrane 100 may be between about 30 µm (0.03 mm) and about 200 µm (0.2 mm), for example between about 30 µm and about 150 µm, between about 30 µm and about 80 µm, or between about 80 µm and about 200 µm, e.g. about 30 µm, 80 µm, 120 µm or 200 µm.

In the context of various embodiments, the length of the membrane 100, defined along a longitudinal axis of a stent when a peripheral surface of the stent is covered by the membrane 100, may be between about 20 mm and about 100 mm, for between about 20 mm and about 50 mm, between about 50 mm and about 100 mm, or between about 40 mm and about 80 mm, e.g. about 20 mm, about 40 mm, about 60 µm, about 80 mm or about 100 mm.

In various embodiments, the number of flaps formed may depend on the dimensions (e.g. length and diameter) of the membrane 100. In the context of various embodiments, the density of the flaps along a longitudinal axis of the membrane 100 may be between 1 flap per 10 mm (1 flap/10 mm) and 8 flaps/10 mm, for example between 1 flap/10 mm and 4 flaps/10 mm, between 1 flap/10 mm and 2 flaps/10 mm, or between 4 flaps/10 mm and 8 flaps/10 mm. In the context of various embodiments, the density of the flaps along a circumference of the membrane 100 may be between 6 flaps/10 mm and 12 flaps/10 mm, for example between 6 flaps/10 mm and 10 flaps/10 mm, between 6 flaps/10 mm and 8 flaps/10 mm, or between 8 flaps/10 mm and 12 flaps/10 mm.

In the context of various embodiments, the membrane 100 may be a sleeve for covering the peripheral surface of the stent. For example, the membrane 100 may be a sleeve for receiving the stent for covering an outer peripheral surface of the stent. Alternatively, the membrane 100 may be a sleeve receivable by the stent for covering an inner peripheral surface of the stent.

The sleeve may have a tubular shape, for example for receiving a tubular stent or receivable by a tubular stent. In addition, the sleeve may have or may include a tapering shape. However, it should be appreciated that the sleeve may be of any shape, for example corresponding to the shape of the stent. In the context of various embodiments, the sleeve may be elastic or deformable such that the sleeve may be adhered to the peripheral surface of the stent as a result of the pressure or radial force exerted by the sleeve to maintain the sleeve on the peripheral surface of the stent. In various embodiments, the sleeve may be adhered to the peripheral surface of the stent by an adhesive, for example by using glue or a thermosetting polymer. In various embodiments, the sleeve may be adhered to the peripheral surface of the stent by a suture.

In the context of various embodiments, the membrane 100 may be coatable on the peripheral surface of the stent. In other words, the membrane 100 may be formed by application of a coating layer on the peripheral surface of the stent. As an example, the membrane 100 or a layer of the membrane 100 may be deposited to coat or cover the peripheral surface of the stent, for example via a dip coating or a spray coating method. In various embodiments, the membrane 100 may be coated to cover a portion or an area of the peripheral surface of the stent or may be coated to cover at least substantially the entire peripheral surface of the stent.

In the context of various embodiments, the membrane 100 may be a biocompatible membrane, for example including but not limited to polyurethanes and polycarbonate urethanes (e.g. Chronoflex AR). The membrane 100 may be biodegradable or non-biodegradable. The membrane 100 may be deformable.

In the context of various embodiments, the membrane 100 may be or may include a polymeric membrane, a biological membrane or a film of metal.

Figure 1B:
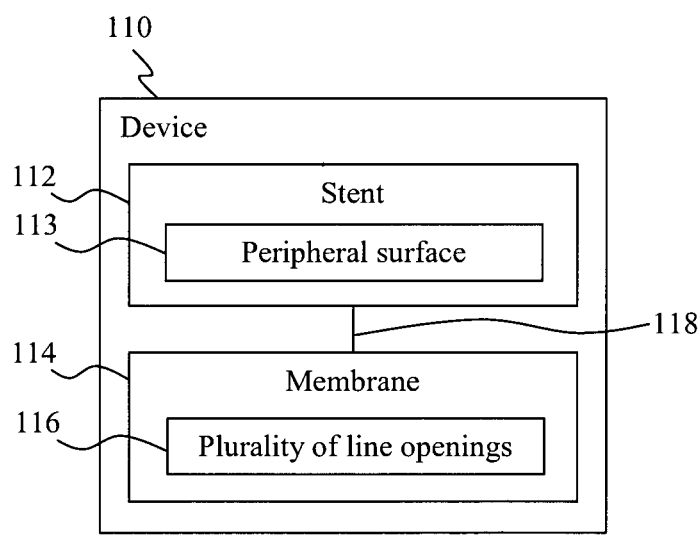
FIG. 1B shows a schematic block diagram of a device for use in a blood vessel, according to various embodiments.

FIG. 1B shows a schematic block diagram of a device 110 for use in a blood vessel, according to various embodiments. The device 110 may include a stent 112 configured to be received in the blood vessel, and a membrane 114 configured to cover a peripheral surface 113 of the stent 112, wherein the membrane 114 includes a plurality of line openings 116 formed therein. The stent 112 is configured to be received in the blood vessel and engaged therewith.

In FIG. 1B, the line represented as 118 is illustrated to show the relationship between the stent 112 and the membrane 114, which may include fluid communication with each other and/or mechanical coupling.

In the context of various embodiments, each line opening 116 may be a straight line opening, for example in the form of a slit, a curved line opening, or any line opening of a suitable shape or curvature, e.g. U-shaped or V-shaped.

In the context of various embodiments, the plurality of line openings 116 may be formed at a portion or an area of the membrane 114 or throughout the membrane 114.

In various embodiments, each line opening 116 may be a straight line opening, for example a slit. The slit may allow a fluid, e.g. blood, to pass through, when the slit is in an open position. As a non-limiting example, as the blood flows through the membrane 114, the pressure gradient of the blood flow may expand slits that are positioned at a side branch of a blood vessel and not against a blood vessel wall, so as to define respective pores or apertures or openings in an open position, through which the blood may flow through, for example, to the side branch of the blood vessel. Where the membrane 114 is positioned against a blood vessel wall, the slits are pushed against the wall and unable to expand, and therefore in a closed position. It should be appreciated that the slits, including their dimensions and other parameters, may be as described in the context of the membrane 100 of FIG. 1A.

In various embodiments, each line opening 116 of the plurality of line openings 116 may be shaped, for example as a curved line opening, to define a partial boundary of a portion of the membrane 114 therewithin, wherein the portion defines a flap. Therefore, the membrane 114 may include a plurality of flaps, each flap corresponding to a line opening 116 that defines a partial boundary of the flap. The plurality of flaps may be formed from part of the membrane 114. In various embodiments, each line opening 116 may be shaped in the form of a curved line opening, for example U-shaped. In, various embodiments, the plurality of flaps may be defined or formed at a portion or an area of the membrane 114 or throughout the membrane 114.

In the context of various embodiments, each flap may be formed in the membrane 114 such that a connecting section of the membrane 114 extending between two ends of the line opening 116 is oriented at least substantially transverse to a longitudinal axis of the stent 112.

In the context of various embodiments, each flap may be pivotable about the connecting section between an open position in which the flap extends outwardly from the membrane 114 thereby defining an opening in the membrane 114, and a closed position in which the flap extends in line with the membrane 114 thereby at least substantially closing said opening. Therefore, the device 110 may be a preferential covered stent such that, for example, the device 110 may allow perfusion of blood through the flaps into a side branch area of a blood vessel, while preventing blood flow through the flaps in a non-branched area of a blood vessel, thereby preventing plaque fragments from getting into the blood circulation.

In various embodiments, the connecting section may be configured to face an inflow end of the stent 112 when placed in the blood vessel. In other words, the blood flows in a direction from the connecting section to the tip of each flap.

In the context of various embodiments, it should be appreciated that the flaps, including their dimensions and other parameters, may be as described in the context of the membrane 100 of FIG. 1A.

In the context of various embodiments, the plurality of line openings 116 may be oriented in a same direction or in different directions, for example parallel to or perpendicular to or at an angle to an axis of the membrane 114 or the stent 112, for example, a transverse axis or a longitudinal axis of the membrane 114 or the stent 112.

In the context of various embodiments, the membrane 114 may be a sleeve for covering the peripheral surface of the stent 112. For example, the membrane 114 may be a sleeve for receiving the stent 112 for covering an outer peripheral surface of the stent 112. Alternatively, the membrane 114 may be a sleeve receivable by the stent 112 for covering an inner peripheral surface of the stent 112.

The sleeve may have a tubular shape, for example for receiving a tubular stent or receivable by a tubular stent. In addition, the sleeve may have or may include a tapering shape. However, it should be appreciated that the sleeve may be of any shape, for example corresponding to the shape of the stent 112. In the context of various embodiments, the sleeve may be elastic or deformable such that the sleeve may be adhered to the peripheral surface 113 of the stent 112 as a result of the pressure or radial force exerted by the sleeve to maintain the sleeve on the peripheral surface 113 of the stent 112. In various embodiments, the sleeve may be adhered to the peripheral surface 113 of the stent 112 by an adhesive, for example by using glue or a thermosetting polymer. In various embodiments, the sleeve may be adhered to the peripheral surface 113 of the stent 112 by a suture.

In the context of various embodiments, the membrane 114 may be coated on the peripheral surface 113 of the stent 112. In other words, the membrane 114 may be formed by application of a coating layer on the peripheral surface 113 of the stent 112. As an example, the membrane 114 or a layer of the membrane 114 may be deposited to coat or cover the peripheral surface 113 of the stent 112, for example via a dip coating or spray coating method. In various embodiments, the membrane 114 may be coated to cover a portion or an area of the peripheral surface 113 of the stent 112 or may be coated to cover at least substantially the entire peripheral surface 113 of the stent 112.

In the context of various embodiments, the membrane 114 may partially cover the peripheral surface 113 of the stent 112 or may at least substantially fully cover the peripheral surface 113 of the stent 112, for example the membrane 114 may cover an entire peripheral surface 113 of the stent 112.

In the context of various embodiments, the membrane 114 may be a biocompatible membrane, for example including but not limited to polyurethanes and polycarbonate urethanes (e.g. Chronoflex AR). The membrane 114 may be biodegradable or non-biodegradable. The membrane 114 may be deformable.

In the context of various embodiments, the membrane 114 may be or may include a polymeric membrane, a biological membrane or a film of metal.

In the context of various embodiments, the stent 112 may be porous.

In the context of various embodiments, the stent 112 may be a bare-metal stent, a bare polymeric stent, an alloy stent or a drug-eluting stent. However, it should be appreciated that any other types of stents may be used.

In various embodiments, the bare-metal stent may include a mesh of wires or a matrix of wires. The bare-metal stent may include one of stainless steel, an alloy of cobalt-chromium or nitinol (nickel-titanium). The bare-metal stent may be balloon expandable (e.g. expandable with the aid of a balloon) or self expandable.

In the context of various embodiments, the stent 112 may be biodegradable or non-biodegradable. The stent 112 may be of a synthetic material, e.g. a polymeric material. As a non-limiting example, the stent 112 may be a biodegradable polymeric stent.

In the context of various embodiments, the stent 112 may be a covered stent, such that the stent 112 (e.g. a metal stent) may be pre-covered by a covering material, which may be in the form of a thin layer or a thin film. The covering material may be a membrane (e.g. a polymeric membrane or a biological membrane) or a thin film of metal.

In embodiments where the stent 112 is a covered stent, the membrane 114 may be configured to cover a peripheral surface of the covered stent or arranged over the covering material of the covered stent. Alternatively, the plurality of line openings 116 may be formed in the covering material of the covered stent. In other words, the covering material of the covered stent may include a plurality of line openings formed therein, which may be as described in the context of the plurality of line openings 102, 116.

As non-limiting examples, the covered stent may have a covering material with substantially large pores or windows which may allow loose fragments (e.g. emboli) to flow through the pores or windows into circulation. Therefore, the membrane 114 may be provided so as to cover a peripheral surface of the covered stent or cover the covering material of the covered stent to transform the covered stent into a preferential covered stent, which minimizes or prevents emboli from being released into circulation while at the same time preserving perfusion of blood into a side branch of the blood vessel.

In addition, the covered stent may be a drug eluting stent having a coating (e.g. a polymer coating) which holds and elutes drug into the wall of the blood vessel, and a plurality of line openings 116 may be formed in this coating or a membrane 114 may be provided so as to cover a peripheral surface of the drug eluting stent or cover the coating of the drug eluting stent.

In the context of various embodiments, the membrane 114 may be as described in the context of the membrane 100, and/or the plurality of line openings 116 may be as described in the context of the plurality of line openings 102, and/or the plurality of flaps of the membrane 114 may be as described in the context of the membrane 100.

Various embodiments may also provide use of the device 110 for treating stenosis of a blood vessel and preventing emboli from being released into the blood circulation, while allowing perfusion of blood into a side branch of the blood vessel.

Various embodiments may also provide use of the device 110 for treating thromboembolic disease of a blood vessel while allowing perfusion of blood into a side branch of the blood vessel.

Figure 1C:
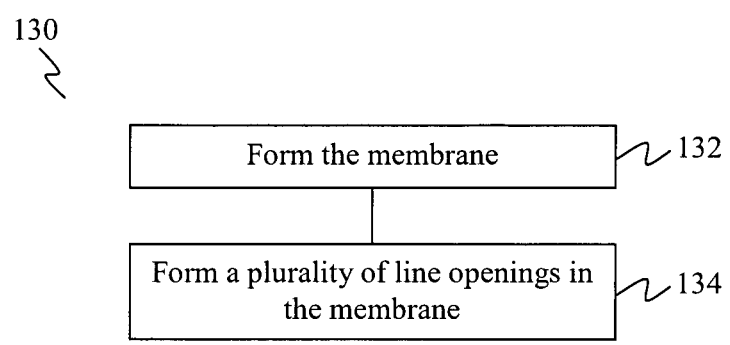
FIG. 1C shows a flow chart illustrating a method of forming a membrane on a stent, according to various embodiments.

FIG. 1C shows a flow chart 130 illustrating a method of forming a membrane on a stent, according to various embodiments.

At 132, the membrane is formed on a peripheral surface of the stent.

At 134, a plurality of line openings are formed in the membrane.

In various embodiments, at 132, the stent may be expanded in a radial direction, and the membrane is formed on the peripheral surface of the expanded stent. The plurality of line openings may be formed in the membrane formed on the peripheral surface of the expanded stent.

By forming the plurality of line openings in the membrane when the stent is in an expanded configuration, the plurality of line openings are therefore formed when the membrane is in the expanded configuration. Therefore, in the expanded configuration, the plurality of line openings are in a closed position, with minimal width/gap.

In various embodiments, the membrane may be expanded to a size or diameter that is comparable to the diameter of the blood vessel where the membrane is intended to be inserted or to a diameter intended for the membrane when the membrane is in use in the blood vessel, or the membrane may be over-expanded to a size or diameter that is larger than the diameter intended for the membrane when the membrane in use in the blood vessel. As a non-limiting example, where the diameter of the membrane when in use in the blood vessel is about 7 mm, the membrane may be expanded to about 8 mm when forming a plurality of line openings in the membrane. In this way, when the membrane is in use in the blood vessel, the membrane is in a slightly contracted configuration as compared to the over-expanded configuration when the plurality of line openings are formed, and therefore, portions of the membrane on opposing sides of each line opening may be urged towards each other, or the portions may overlay or overlap each other, so as to provide a relatively tight closure of the line opening, when the membrane is in use in the blood vessel.

In various embodiments, at 132, the membrane may be formed so as to partially cover the peripheral surface of the stent or at least substantially fully cover the peripheral surface of the stent, for example the membrane may cover an entire peripheral surface of the stent.

In various embodiments, at 132, the method may include coating the membrane on the peripheral surface of the stent.

In various embodiments, at 134, the method may include shaping each line opening of the plurality of line openings to define a partial boundary of a portion of the membrane therewithin, wherein the portion defines a flap.

In the context of various embodiments, the plurality of line openings, when in the closed position or substantially closed position, may have a width or gap of between about 0.1 µm and about 100 µm, for example between about 0.1 µm and about 50 µm, between about 0.1 µm and about 10 µm, between about 0.1 µm and about 5 µm, e.g. about 0.1 µm, about 1 µm, about 3 µm, about 5 µm, about 10 µm, about 50 µm or about 100 µm. In further embodiments, when in the closed position, there may be pressures acting on the plurality of line openings, for example portions of the membrane on opposing sides of each line opening may be urged towards each other, or the portions may overlay or overlap with each other, so as to provide a relatively tight closure of the line opening.

In any case, the plurality of line openings may be formed so that the width/gap thereof, when the line openings are in the closed position or at least substantially closed position, are smaller than emboli or the width/gap thereof is of the size of about 100 µm, about 50 µm, about 10 µm, about 5 µm or about 3 µm, so as to prevent such emboli from entering the blood circulation.

The plurality of line openings may be formed by making cuts in the membrane, with minimal material loss from the membrane. Therefore, each line opening may have minimal width/gap. In the context of various embodiments, the line openings may be created in the membrane by using a sharp blade or a laser to cut through the membrane. The cuts may be made at a right angle to the membrane (e.g. a laser beam being directed perpendicular to the membrane) or at an oblique angle to the membrane. In various embodiments, cutting through the membrane at an oblique angle to the membrane may produce a flap having a perimeter edge that is angled through the thickness of the membrane. In this way, when a peripheral surface of a stent is covered with the membrane, the flap of the membrane may act as a one-way valve that may extend outwardly from the stent, but which is prevented by the angled perimeter edge to extend inwardly of the stent.

In various embodiments, in a non-expanded configuration, the membrane is in a stress-free or tension-free state and may have a diameter of between about 2 mm and about 3 mm, for example between about 2 mm and about 2.5 mm or between about 2.5 mm and about 3 mm, e.g. a diameter of about 2 mm or about 2.5 mm.

It should be appreciated that a similar method or cutting procedure for forming the plurality of lines openings in a membrane as described above may be applicable for forming a plurality of line openings directly in a stent tube.

The membrane formed by the methods of various embodiments may be as described in the context of the membrane 100.

Various embodiments may provide a membrane for covering a peripheral surface of a stent, where the membrane includes a plurality of flaps formed therein. Each flap may be pivotable between an open position in which the flap extends outwardly from the membrane thereby defining an opening in the membrane, and a closed position in which the flap extends in line with the membrane thereby at least substantially closing said opening. Each flap may be formed in the membrane with a connecting section of the membrane extending between two ends of the line opening. Therefore, the connecting section joins the flap to the membrane. It should be appreciated that the membrane and the plurality of flaps may be as described in the context of the membrane 100. Therefore, the membrane, when used for covering a peripheral surface of a stent (e.g. a bare-metal stent), may provide a preferential covered stent. In various embodiments, a corresponding method of forming a membrane on a stent may be provided, which may include forming the membrane, and forming a plurality of flaps in the membrane.

Various embodiments may further provide a covered stent where a stent is moulded or embedded into a membrane, where the membrane includes a plurality of line openings formed therein. The membrane may cover a peripheral surface of the stent.

Various embodiments may further provide a stent including a plurality of line openings formed therein. The line openings may be in the form of slits, or may define respective partial boundaries of flaps. In one embodiment, the stent may be or may include a metal tube and the plurality of lines may be carved or cut from the metal tube. The metal tube, for example, may be made of nitinol (nickel-titanium). In further embodiments, the stent may be or may include a tube of a synthetic material, e.g. a polymeric tube, and the plurality of line openings may be cut or formed in the tube. The polymeric tube may be biodegradable. Therefore, the tube may include a plurality of line openings formed therein, such that the tube acts as both a stent and a membrane. In other words, the plurality of line openings are formed from part of the tube. Therefore, a unitary component or material may be employed to provide an integrated supporting structure having line openings formed therein. The plurality of line openings, defining slits or flaps, may be similar to that as described in the context of the membranes 100, 114.

Figure 2A:
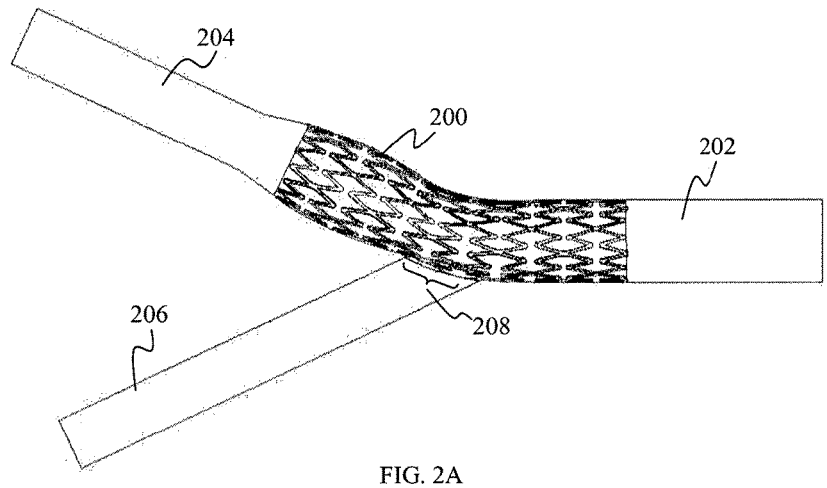
FIG. 2A shows a schematic view of a stent covered with a membrane positioned over the carotid bifurcation region, according to various embodiments.

FIG. 2A shows a schematic view of a stent with a membrane covering a peripheral surface of the stent (the stent and the membrane collectively represented as 200), positioned over the carotid bifurcation region, according to various embodiments. While not clearly shown, the membrane may cover the outer peripheral surface of the stent. However, it should be appreciated that the membrane may instead cover the inner peripheral surface of the stent. The covered stent 200, may be placed through at least a portion of the common carotid artery (CCA) 202 and at least a portion of the internal carotid artery (ICA) 204, and across the external carotid artery (ECA) 206. Therefore, the covered stent 200 are positioned against the wall of the common carotid artery (CCA) 202 and that of the internal carotid artery (ICA) 204, except for a portion, as indicated by 208, facing an entrance of the external carotid artery (ECA) 206 to allow perfusion of blood into the external carotid artery (ECA) 206.

As an example, the covered stent 200 may be placed over a diseased carotid bifurcation along a blood vessel (e.g. the internal carotid artery (ICA) 204) to prevent emboli from being released into blood circulation, while over the site 208 where the external carotid artery (ECA) 206 branches out from the common carotid artery (CCA) 202, the covered stent 200 may enable side branch perfusion to allow blood flow from the common carotid artery (CCA) 202 to the external carotid artery (ECA) 206.

Figure 2B:
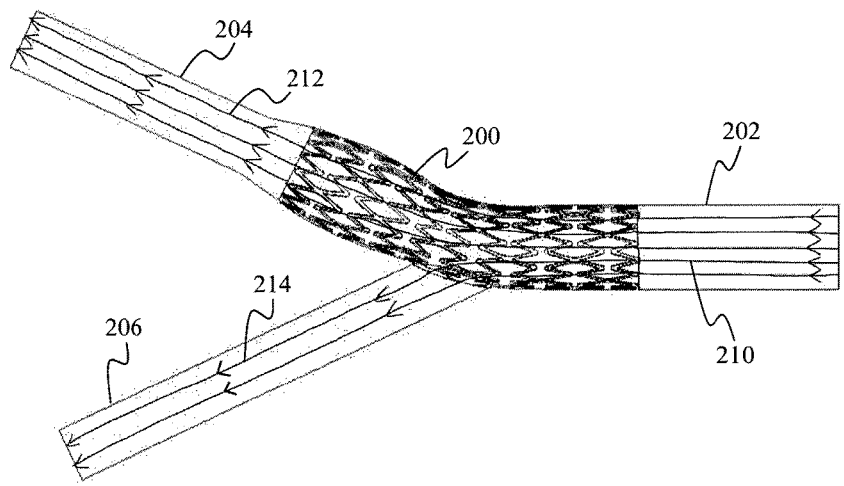
FIG. 2B shows the flow streamlines through the carotid bifurcation region illustrated in FIG. 2A.

FIG. 2B shows the flow streamlines 210, 212, 214, through the carotid bifurcation region illustrated in FIG. 2A. As a non-limiting example, the covered stent 200 may include a membrane having a plurality of slits. As illustrated in FIG. 2B, the flow streamline 210 through the CCA 202 may partially flow (represented as flow streamline 212) into and through the ICA 204, as well as partially flow (represented as flow streamline 214) through the slits of the membrane of the covered stent 200 into the ECA 206.

Various embodiments may provide a biocompatible membrane (such as polyurethanes and polycarbonate urethanes (e.g. Chronoflex AR)), on which line openings, for example in the form of slits, or defining respective partial boundaries of flaps, may be cut (e.g. using a blade or a laser) through the membrane. The membrane may be provided to cover a peripheral surface of a stent, and the slits or the flaps of the membrane may be formed in between the struts of the stent, in each cell of the stent. In the context of various embodiments, there is minimal material loss from the membrane when making the cut in the membrane to form the plurality of line openings In the context of various embodiments, the struts of a stent refer to the support elements of the stent, for example the struts of a bare metal stent refer to the mesh of metal wires forming the bare metal stent. In the context of various embodiments, a stent cell refers to a region of the stent, the region having its perimeter bounded by the struts of the stent.

Figure 3A:
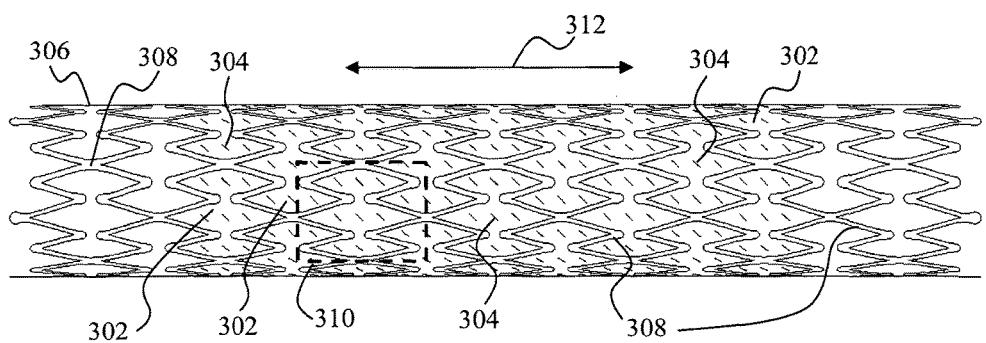
FIG. 3A shows a schematic side view of a membrane with slits covering an inner peripheral surface of a stent, according to various embodiments.

FIG. 3A shows a schematic side view of a membrane 302 with slits 304 covering an inner peripheral surface of a stent 306 having struts 308, according to various embodiments. However, it should be appreciated that the membrane 302 may instead cover an outer peripheral surface of the stent 306. It should be appreciated that the stent 306 and the membrane 302 are continuous structures, and may have circular cross sections.

The slits 304 may be formed or cut at areas of the membrane 302 corresponding to areas of the stent 306 in between the struts 308 of the stent 306 in each cell 310 of the stent 306. The double-headed arrow 312 illustrates the longitudinal axis of the membrane 302 and also that of the stent 306. The stent 306 and the membrane 302 may be expandable in a direction transverse to the longitudinal axis 312.

While FIG. 3A illustrates that only a portion of the inner peripheral surface of the stent 306 is covered by the membrane 302 having slits 304, it should be appreciated that the entire inner peripheral surface of the stent 306 may be covered by the membrane 302. The slits 304 may be formed throughout the membrane 302 or on portions of the membrane 302.

Figure 3B:
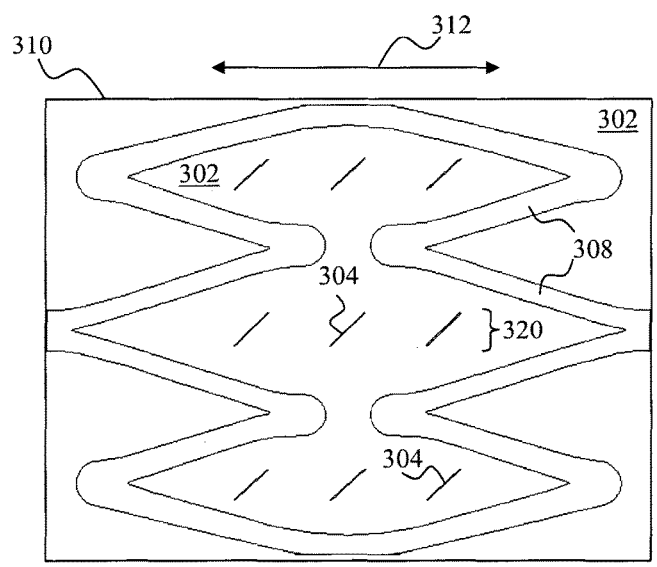
FIGS. 3B to 3D show schematic side views of membranes with slits in different orientations, respectively, for a single stent cell of the covered stent of various embodiments.
Figure 3C:
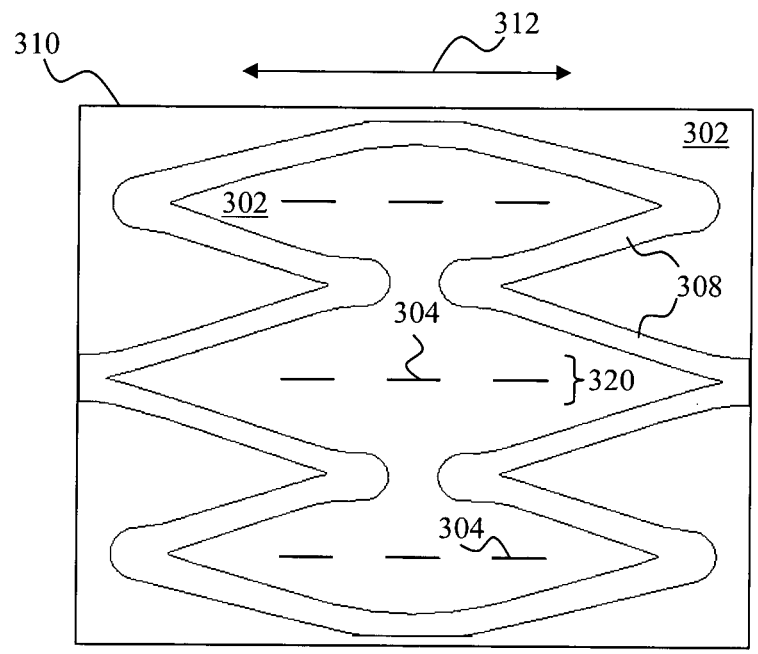
Figure 3D:
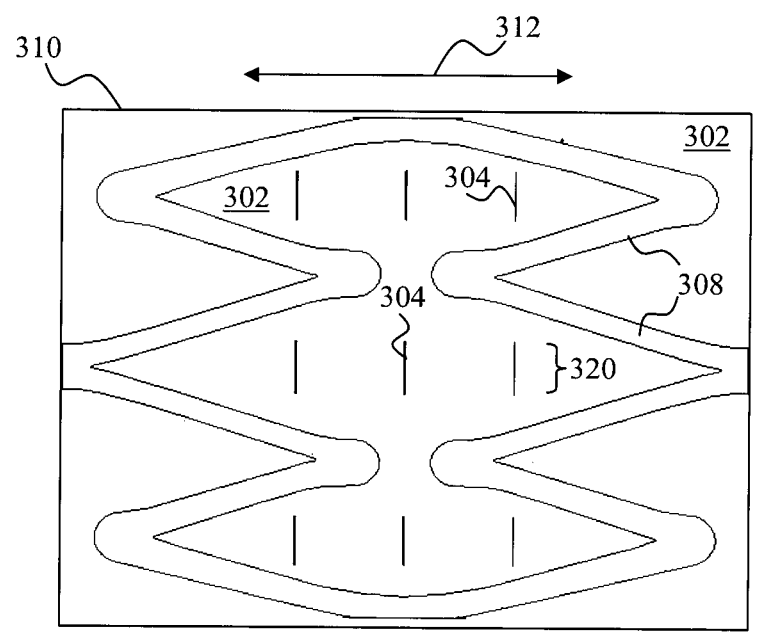

FIGS. 3B to 3D show schematic side views of membranes 302 with slits 304 in different orientations, respectively, for a single stent cell 310 of the covered stent of various embodiments. FIG. 3B shows that the slits 304 may be oriented at an angle to the longitudinal axis 312 of the stent 306. FIG. 3C shows that the slits 304 may be oriented parallel to the longitudinal axis 312 of the stent 306. FIG. 3D shows that the slits 304 may be oriented perpendicular to the longitudinal axis 312 of the stent 306.

While each of FIGS. 3B to 3D illustrates that the slits 304 are oriented in the same direction or orientation for each embodiment, it should be appreciated that the slits may also be oriented in different directions or orientations relative to each other, for example based on any combination of the orientations of the slits 304 illustrated in FIGS. 3B to 3D.

While FIGS. 3B to 3D illustrate three slits 304 per row 320, it should be appreciated that any number of slits 304 per row 320 may be provided, for example, one, two, four, five or any higher number of slits 304. In addition, while FIGS. 3B to 3D illustrate that the slits 304 are arranged in rows 320, it should be appreciated that the slits 304 may be arranged in any periodic, non-periodic or random array.

Figure 3E:
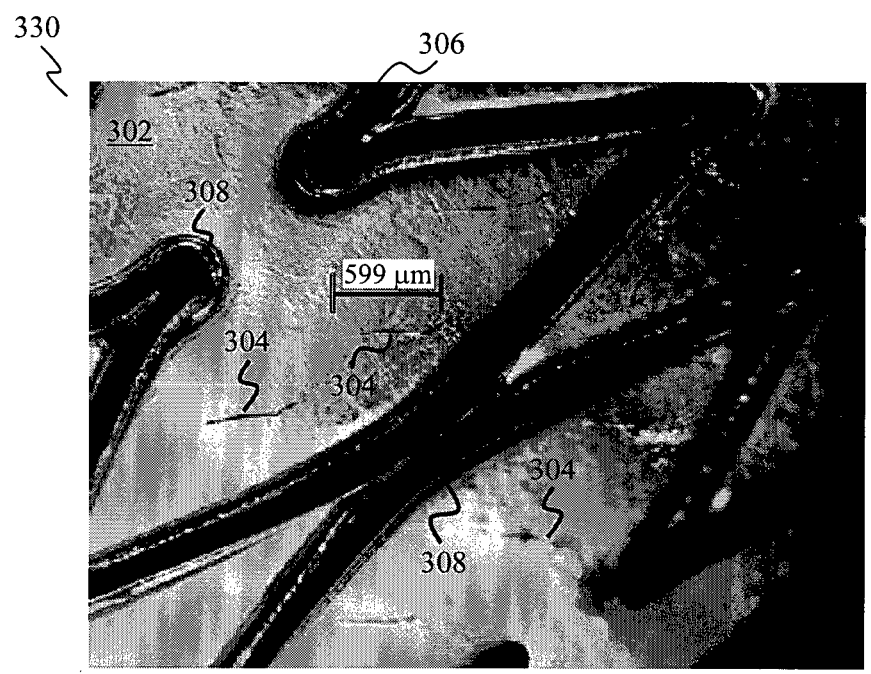
FIG. 3E shows a microscopic image of a membrane with slits covering an inner peripheral surface of a stent, according to various embodiments.

FIG. 3E shows a microscopic image 330 of a membrane 302 with slits 304 covering an inner peripheral surface of a stent 306, according to various embodiments. As illustrated in FIG. 3E, the slits 304 have lengths of about 600 μm.

In various embodiments, the stent 306 and the membrane 302 covering an inner peripheral surface of the stent 306 may be positioned in a blood vessel. At a non-branched site of the blood vessel, the slits 304 of the membrane 302 are positioned against the wall of the blood vessel and do not open or expand, even when there is blood flowing through the stent 306 placed into the blood vessel, as the slits 304 are opposed against the wall and therefore in the closed position. In this closed position, the membrane 302 acts as a barrier to contain any loose materials between the membrane 302 and the inner surface of the wall of the blood vessel.

At a side-branched site of the blood vessel, the slits 304 of the membrane 302 are positioned at the entrance of the side branch, facing the side branch, where these slits 304 may open or expand to define pores or openings, due to the pressure of the blood flowing through the stent 306 placed into the blood vessel, and therefore blood may flow through the pores into the side branch.

Accordingly, the stent 306 having the membrane 302 including a plurality of slits 304 may act as a preferential covered stent. The slits 304 may allow blood flow through the membrane 302 into a side branch (e.g. ECA) of a blood vessel, where the slits 304 face the side branch, and at portions of the blood vessel without a side branch, the slits 304 face the lumen wall of the blood vessel where the membrane 302 provides a covering to confine the atherosclerotic plaques and minimize or prevent their release into the blood flow, as the slits 304 may not open in non-branched regions and therefore the atherosclerotic plaques may not pass through the slits 304 and through the stent 306 into the blood stream or circulation.

Figure 4A:
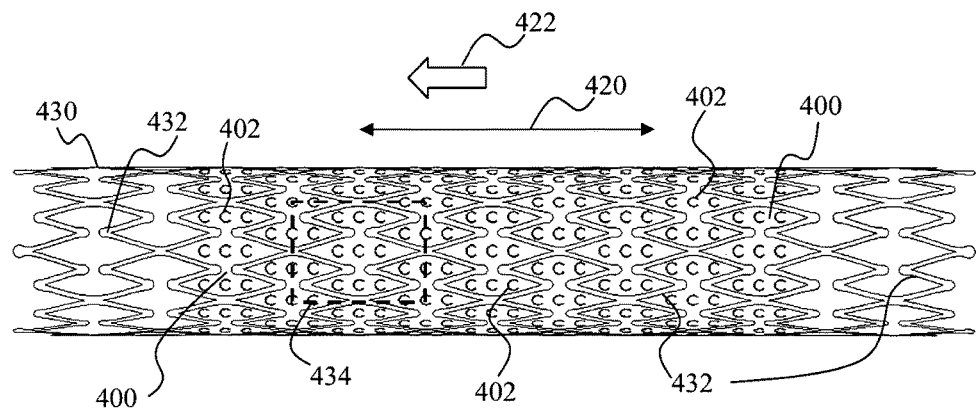
FIG. 4A shows a schematic side view of a membrane with flaps covering an inner peripheral surface of a stent, according to various embodiments.

FIG. 4A shows a schematic side view of a membrane (e.g. a biocompatible membrane) 400 with flaps 402 covering an inner peripheral surface of a stent 430 having struts 432, according to various embodiments. However, it should be appreciated that the membrane 400 may instead cover an outer peripheral surface of the stent 430. While not clearly shown, it should be appreciated that the stent 430 and the membrane 400 are continuous structures, and may have circular cross sections.

Figure 4B:
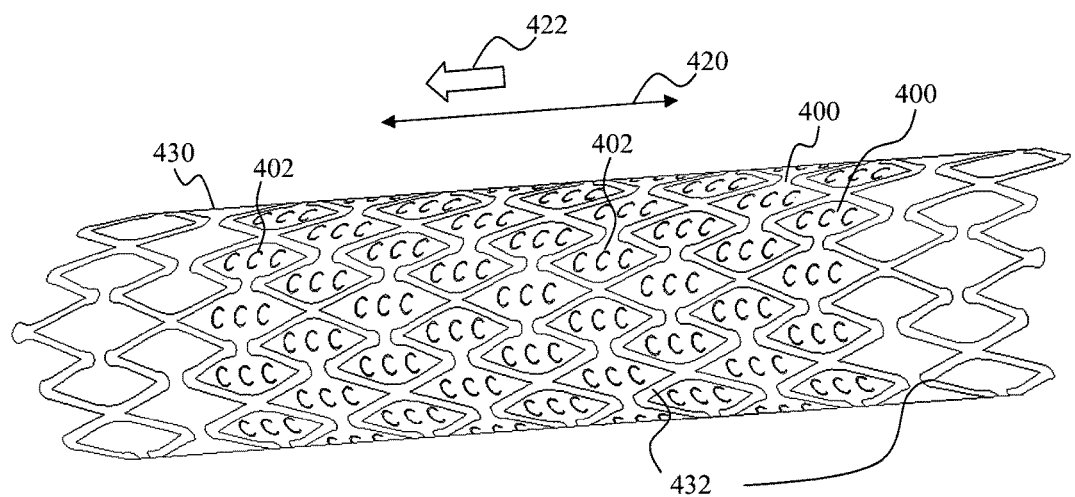
FIG. 4B shows a schematic perspective view of a portion of the covered stent of the embodiment of FIG. 4A.
Figure 4C:
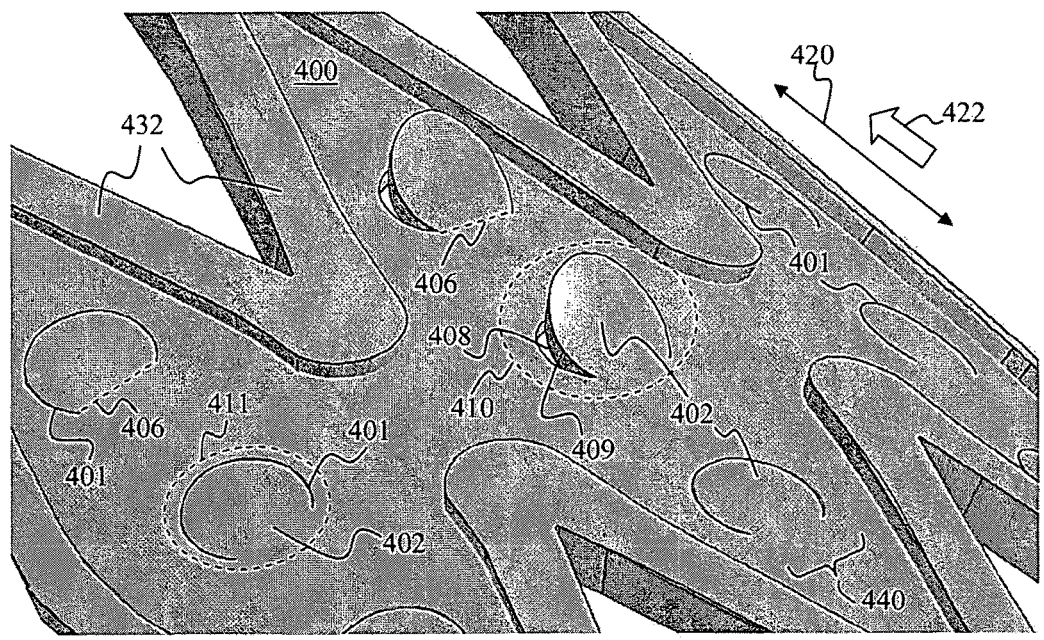
FIG. 4C shows an enlarged schematic view illustrating the flaps formed in the membrane for a single stent cell of the covered stent of the embodiment of FIG. 4A.

FIG. 4B shows a schematic perspective view of a portion of the covered stent of the embodiment of FIG. 4A, while FIG. 4C shows an enlarged schematic view illustrating the flaps 402 formed in the membrane 400 for a single stent cell 434 of the covered stent of the embodiment of FIG. 4A.

While FIGS. 4A and 4B illustrate that only a portion of the inner peripheral surface of the stent 430 is covered by the membrane 400 having flaps 402, it should be appreciated that the entire inner peripheral surface of the stent 430 may be covered by the membrane 400. The flaps 402 may be formed throughout the membrane 400 or on portions of the membrane 400.

Referring to FIGS. 4A to 4C, the membrane 400 includes a plurality of line openings 401, where each line opening 401 is shaped to define a partial boundary of a portion of the membrane 400 therewithin, which defines a flap 402. Therefore, the membrane 400 includes a plurality of flaps 402, for example having an arrangement of densely patterned flaps 402 formed therein.

The plurality of flaps 402 may be diffusely and densely distributed on the membrane 400. The plurality of flaps 402 may be formed over a substantial portion of the membrane 400, and/or in a central portion of the membrane 400, and/or in a regular configuration in a grid-like pattern. However, it should be appreciated that the plurality of flaps 402 may be formed at any portion of the membrane and/or at any sized portion of the membrane 400, including at least substantially the entire membrane 400, and/or in any configuration, in a periodic or non-periodic pattern.

The flaps 402 may be formed at areas of the membrane 400 corresponding to areas of the stent 430 in between the struts 432 of the stent 430 in each cell 434 of the stent 430. The double-headed arrow 420 illustrates the longitudinal axis of the membrane 400 and also that of the stent 430. The stent 430 and the membrane 400 may be expandable in a direction transverse to the longitudinal axis 420.

Each flap 402 may be formed in the membrane 400 with a connecting section (represented by the dashed line 406) joining the flap 402 to the membrane 400, the connecting section 406 extending between two ends of the line opening 401. As illustrated in FIG. 4C, the line opening 401 defines a partial boundary of the flap 402.

The connecting section 406 of each flap 402 may extend at least substantially transverse to the longitudinal axis 420 of the membrane 400 or of the stent 430. The connecting section 406 of each flap 402 may face an inflow end of the stent 430 when the stent 430 is placed in the blood vessel. The block arrow 422 represents the flow direction of blood in the blood vessel when the stent 430 with the membrane 400 is placed in the blood vessel. In other words, the flaps 402 are designed and oriented such that the connecting sections 406 (or attached parts) of the flaps 402 are at an inflow side of blood flow and the movable parts of the flaps 402 are at the outflow side of blood flow.

Each flap 402 is pivotable about the connecting section 406 between an open position in which the flap 402 extends outwardly from, the membrane 400 thereby defining an opening 408 in the membrane 400 (e.g. a flap 402 in the open position is indicated by the dashed circle 410), and a closed position in which the flap 402 extends in line with the membrane 400 thereby at least substantially closing said opening 408 (e.g. a flap 402 in the closed position is indicated by the dashed circle 411).

As illustrated in FIG. 4C, each flap 402 may have a perimeter edge 409 that is angled through the thickness of the membrane 400, for example where the line opening 401 is formed by making a cut at an oblique angle to the membrane 400. In this way, each flap 402 may act as a one-way valve that may extend outwardly from the stent 430, but which is prevented by the angled perimeter edge 409 to extend inwardly of the stent 430.

Depending on the configuration of the flaps 402, the pressure gradient of the blood flow and the positions of the flaps 402, e.g. whether the membrane 400 and the corresponding flaps 402 are opposed towards a blood vessel wall, the flaps 402 may be in the closed position or pivot between the open position and the closed position, for example as a result of the pulsatile blood flow.

The respective flaps 402 may be in the open position to allow blood flowing through the stent 430, with its inner peripheral surface covered by the membrane 400, to flow through the respective flaps 402, for example, into a side branch section of the blood vessel. In addition, the respective flaps 402 may be in the closed position to prevent blood flowing through the stent 430 to flow through the respective flaps 402 when, for example, the respective flaps 402 are adjacent to an inner wall of the blood vessel. This may occur for example at a non-branched section of the blood vessel where the inner wall of the blood vessel prevents the respective flaps 402 from opening, thereby preventing blood from flowing through the membrane 400. Therefore, at a non-branched section of the blood vessel, the respective flaps 402 are pushed against the inner wall of the blood vessel. Accordingly, the membrane 400 and the respective closed flaps 402 act as a barrier between the inner wall and the blood flow inside the lumen of the blood vessel. In addition, the membrane 400 and the respective closed flaps 402 may trap any emboli against the inner wall of the blood vessel.

While each of FIGS. 4A to 4C illustrates that the flaps 402 are oriented in the same direction or orientation with the connecting section 406 of each flap 402 extending transversely to the longitudinal axis 420, it should be appreciated that the flaps 402 may also be oriented in a different direction or orientation, for example with the connecting section 406 of each flap 402 oriented at an angle to the longitudinal axis 420. In addition, different flaps 402 formed in the membrane 400 may be oriented in different orientations.

While FIGS. 4A to 4C illustrate three flaps 402 per row 440, it should be appreciated that any number of flaps 402 per row 440 may be provided, for example, one, two, four, five or any higher number of flaps 402. In addition, while FIGS. 4A to 4C illustrate that the flaps 402 are arranged in rows 440, it should be appreciated that the flaps 402 may be arranged in any periodic, non-periodic or random array.

Figure 4D:
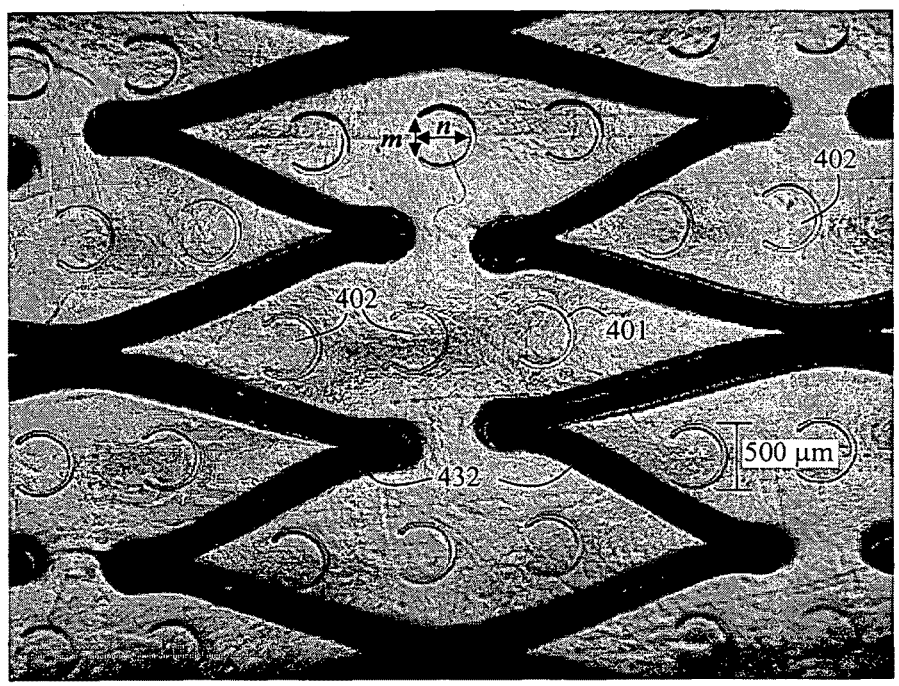
FIGS. 4D to 4F show microscopic images of membranes with flaps of different shapes, respectively, in a closed position, for a single stent cell of the covered stent of various embodiments. Each membrane covers an inner peripheral surface of the stent.

Furthermore, it should be appreciated that each flap 402 may have any suitable shape. As a non-limiting example, each line opening 401 may be shaped to define an arc of a circle such that the flap 402 defines a sector of a circle and having a particular radius of curvature, for example as shown in FIG. 4D. As illustrated in FIG. 4D, each line opening 401 may be shaped to define an arc of a circle with a diameter of about 500 μm.

Figure 4E:
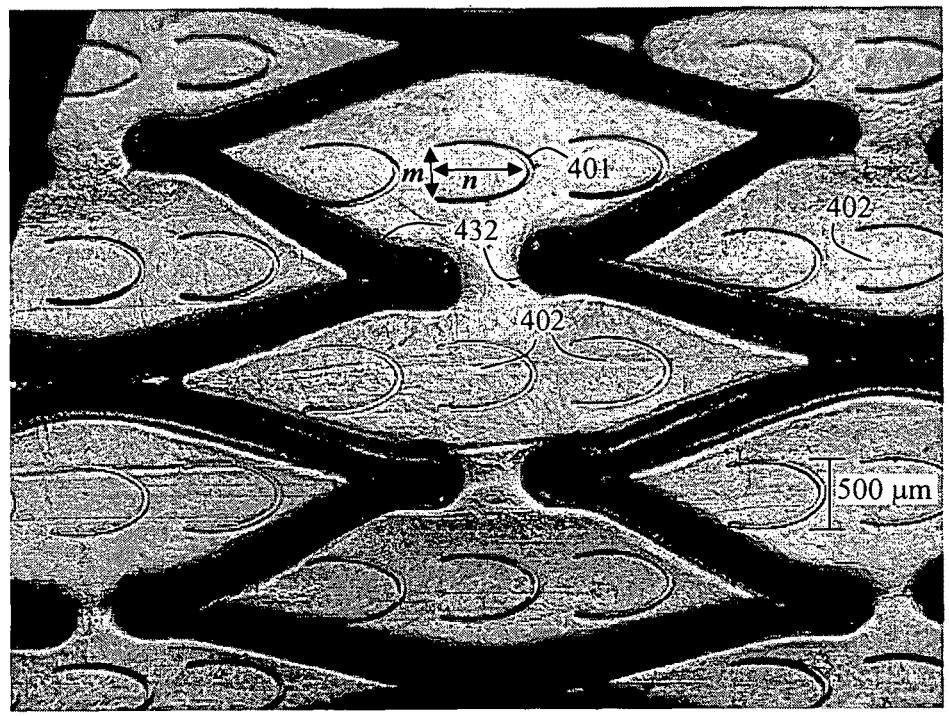

In further embodiments, each line opening 401 may be shaped such that the corresponding flap 402 has an ellipsoidal shape (FIG. 4E), a rectangular shape, a triangular shape having a vertex defining a tip of the flap 402, with the vertex positioned centrally or off-centrally of the flap 402, a trapezoidal shape having a base side parallel to the connecting sections 406, and lateral non-parallel sides diverging away from each other or one lateral side diverging away from the other non-parallel lateral side that is formed perpendicularly to the base of the trapezoidal shape. As illustrated in FIG. 4E, each line opening 401 is shaped such that the corresponding flap 402 has an ellipsoidal shape with a diameter of about 500 μm along the minor axis of the ellipse.

Figure 4F:
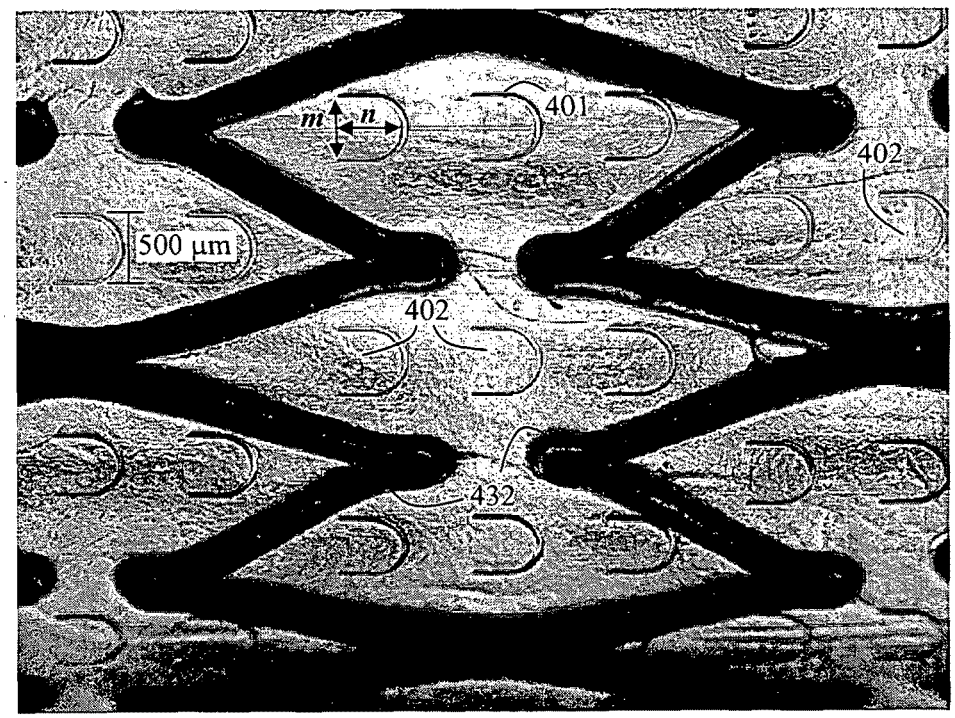

In further embodiments, each line opening 401 may be shaped to have two opposing sides (e.g. parallel lines or lines diverging away from each other) that may then adjoin to each other in the form of a curved line (e.g. a circular arc or U-shaped or V-shaped). In FIG. 4F, each line opening 401 is shaped to have two opposing parallel lines which adjoin to each other by a curved line shaped to define an arc of a circle with a diameter of about 500 μm.

In addition, it should be appreciated that the plurality of flaps 402 may be arranged in any configuration. As a non-limiting example, the plurality of flaps 402 may be arranged in a grid-like pattern, having multiple rows and columns of flaps 402, for example in the form of a square array or a rectangular array. The plurality of flaps 402 may also be arranged in the form of a staggered array, where the central axis of the flaps 402 arranged in a row (or column) are offset from the central axis of the flaps 402 arranged in the preceding and/or succeeding rows (or columns). However, it should be appreciated that the plurality of flaps 402 may be arranged in any configuration, periodically or non-periodically or randomly.

Figure 5A:
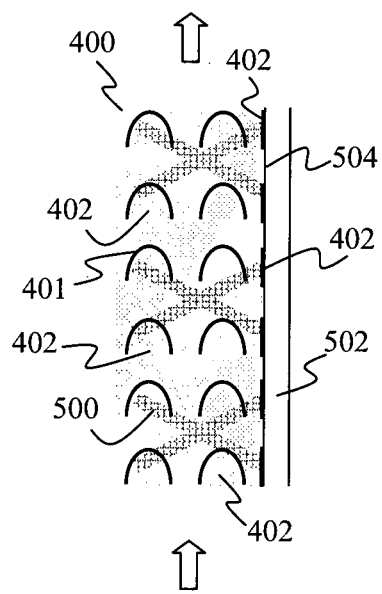
FIGS. 5A and 5B show schematic partial cross sectional views illustrating operations of a membrane having a plurality of flaps, when opposed against a blood vessel wall in a non-branched section of the blood vessel, and in a blood vessel with a side branch respectively, according to various embodiments.
Figure 5B:
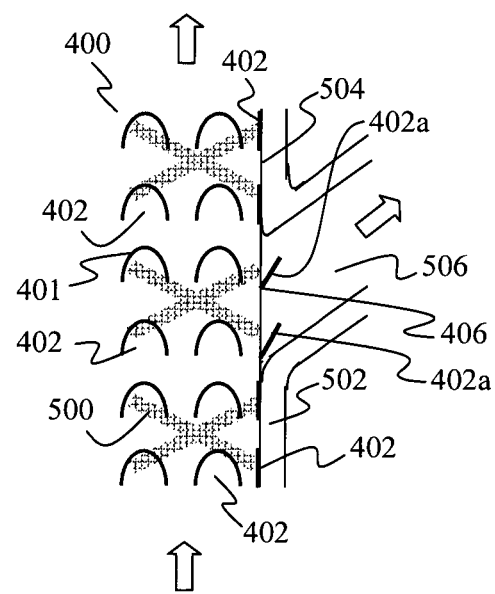

FIGS. 5A and 5B show schematic partial cross sectional views illustrating operations of a membrane 400 having a plurality of flaps 402, along a longitudinal axis of a blood vessel, according to various embodiments. As illustrated in FIGS. 5A and 5B and as a non-limiting example, a stent 500 is received by the membrane 400 to cover an outer peripheral surface of the stent 500, and placed in a blood vessel having a blood vessel wall 502. However, it should be appreciated that the membrane 400 may cover an inner peripheral surface of the stent 500. In FIGS. 5A and 5B, the block arrows illustrate the blood flow directions.

In FIG. 5A, the stent 500 and the membrane 400 are positioned in a blood vessel without a side branch. While not shown, the wall 502 of the blood vessel surrounds the stent 500 and the membrane 400. In other words, the flaps 402 of the membrane 400 are positioned against the wall 502 and are prevented from opening, even when there is blood flowing through the stent 500 placed in the blood vessel, as the flaps 402 are opposed against the wall 502 and therefore in the closed position. In this closed position, the membrane 400 acts as a barrier to contain any loose materials between the membrane 400 and the inner surface 504 of the wall 502 of the blood vessel.

In FIG. 5B, the stent 500 and the membrane 400 are positioned in a blood vessel with a side branch (e.g. ECA) 506. While not shown, the wall 502 of the blood vessel surrounds the stent 500 and the membrane 400, except at the entrance of the side branch 506 where the flaps 402a face the side branch 506. Therefore, the flaps 402a of the membrane 400 positioned facing the side branch 506 may open or extend outwardly from the membrane 400, due to the pressure gradient of the blood flowing through the stent 500, and therefore blood may flow through the open flaps 402a into the side branch 506. At other positions other than at the side branch 506, the flaps 402 of the membrane 400 are positioned against the wall 502 and are prevented from opening, even when there is blood flowing through the stent 500, as the flaps 402 are opposed against the wall 502 and therefore in the closed position.

Accordingly, when the stent 500 covered with the membrane 400 is deployed over a branch site of a blood vessel, the flaps' partially open configuration, as a result of the line openings 401 partially separating the flaps 402 from the membrane 400, and/or the pressure gradient of the blood flow may cause the flaps 402 to open and extend outwardly from the membrane 400, thereby allowing and maintaining perfusion of blood to the side branch 506.

Therefore, the stent 500 having the membrane 400 including a plurality of flaps 402 may act as a preferential covered stent.

In various embodiments, the membrane material property and design of the flaps 402 may be optimized or chosen so as to ensure that each of the plurality of flaps 402 may be configured to be pivotable between the open position and the close position under a wide range of blood pressure. The range of blood pressure includes the systolic pressure and the diastolic pressure of a living human being.

Various embodiments provide a membrane for covering a peripheral surface of a stent and a device (e.g. a covered carotid stent) which may address the issue that carotid stenosis is an embolic disease rather than purely obstructive disease. Thus, various embodiments and the associated treatments aim to refrain or minimise the release of small atheroma fragments into the blood circulation not only during the intervention carotid artery stenting (CAS) procedure, but also for a long period of time after the stenting procedure, for example at least until the atherosclerotic plaque is stabilized.

Various embodiments may provide a covered carotid stent that may be superior to or an improvement over conventional covered stents which seal off any opening in between the struts of a stent with a membrane, and which do not allow blood flow to any side branch of a blood vessel. The covered carotid stent of various embodiments is also different from conventional covered stents with porosity of the membrane, as porosity is a material property rather than mechanically created line openings, for example slits and flaps. The covered carotid stent of various embodiments is also different from and superior to or an improvement over conventional covered stents with a window opened over a particular region of the stent, with which the window has to be aligned exactly with the side branch (e.g. ECA) to enable side branch perfusion, where such an alignment is not an easy task.

Various embodiments may provide for treatment of carotid artery stenosis. Carotid artery stenosis, with atherosclerosis affecting the carotid artery, usually at the carotid bifurcation region, causes ischemic stroke by embolic event. Various embodiments may provide a stent supported barrier (e.g. a membrane with a plurality of line openings formed therein, e.g. either slits and/or flaps formed therein) that may constrain the friable atherosclerotic plaque over the inner wall of carotid artery, for example at a non-branched area of the carotid artery. At the same time, as the plurality of line openings open over the side branch area, perfusion of blood to the branched area of the carotid artery, e.g. external carotid artery (ECA), may be preserved. Therefore, in treating stenosis of a blood vessel over a non-branched area of the blood vessel, the stent covered with a membrane, according to various embodiments, may allow blood to flow through the blood vessel within the non-branched section (e.g. CCA and ICA) of the blood vessel while preventing emboli from being dislodged from the blood vessel and circulating in the bloodstream, and also at the same time allowing blood to flow into a side branch (e.g. ECA) of the blood vessel.

Various embodiments, besides treating carotid artery stenosis, may also be applied to intra-cranial atherosclerotic disease of vessel that has a side branch, as well as other therapies, e.g. for lower limb arteries. Various embodiments may also be used for treating atherosclerotic disease in aorta which may cause emboli to be released to the distal circulation.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A membrane for covering a peripheral surface of an expandable stent configured to be received in a blood vessel, the membrane comprising a single layer having a plurality of line openings formed therein, each line opening comprising a slit or a flap and being configured for:
    allowing, in an open state when covering the expanded stent in the blood vessel, blood from outside a lumen of the stent to flow inside the lumen and then out of respective gaps of the plurality of line openings into a branch area of the blood vessel,
    at least substantially closing the gaps in a closed state when the membrane covers the stent and the stent is expanded to the wall of the blood vessel, and
    changing from the closed state to the open state by expanding outwardly away from the expanded stent in response to blood flow in the lumen when the stent is expanded and resides at the branch area within the blood vessel.

2. The membrane as claimed in claim 1, wherein each line opening of the plurality of line openings is shaped to define a partial boundary of a portion of the membrane therewithin, wherein the portion defines a flap.

3. The membrane as claimed in claim 2, wherein each flap is pivotable relative to the membrane between (a) the open position in which the flap extends outwardly from the membrane thereby defining an opening in the membrane, and (b) the closed position in which the flap extends in line with the single layer of the membrane thereby at least substantially closing said opening.

4. The membrane as claimed in claim 1, wherein each line opening of the plurality of line openings is a straight line opening defining a slit, and wherein when the stent is in an expanded state within the blood vessel and each slit is in a closed position, pressures acting on portions of the membrane on opposing sides of each slit urge the portions of the membrane towards each other so as to provide a substantially tight closure of the slit.

5. The membrane as claimed in claim 1, wherein the membrane is a sleeve for receiving the stent.

6. The membrane as claimed in claim 5, wherein the sleeve has a tubular shape.

7. The membrane as claimed in claim 1, wherein the membrane is coatable on the peripheral surface of the stent.

8. A device for use in a blood vessel, the device comprising:
    a stent configured to be received in the blood vessel, the stent comprising a luminal passage for flow of blood in the blood vessel when the stent is received in the blood vessel; and
    a membrane configured to cover a peripheral surface of the stent, wherein the membrane comprises a single layer having a plurality of line openings formed therein, each line opening comprising a slit or flap and being configured for:
        allowing, in an open state when covering the expanded stent in the blood vessel, blood from outside a lumen of the stent to flow inside the lumen and then out of respective gaps of the plurality of line openings into a branch area of the blood vessel,
        at least substantially closing the gaps in a closed state when the membrane covers the stent and the stent is expanded to the wall of the blood vessel, and
        changing from the closed state to the open state by expanding outwardly away from the expanded stent in response to blood flow in the lumen when the stent is expanded and resides at the branch area within the blood vessel.

9. The device as claimed in claim 8, wherein each line opening of the plurality of line openings is shaped to define a partial boundary of a portion of the membrane therewithin, wherein the portion defines a flap.

10. The device as claimed in claim 9, wherein each flap is formed in the membrane such that a connecting section of the membrane extending between two ends of the line opening is oriented at least substantially transverse to a longitudinal axis of the stent.

11. The device as claimed in claim 10, wherein each flap is pivotable relative to the membrane between (a) the open position in which the flap extends outwardly from the stent thereby defining an opening in the membrane, and (b) the closed position in which the flap extends in line with the single layer of the membrane thereby at least substantially closing said opening.

12. The device as claimed in claims 10, wherein the connecting section is configured to face an inflow end of the stent when placed in the blood vessel.

13. The device as claimed in claim 8, wherein each line opening of the plurality of line openings is a straight line opening defining a slit, and wherein when the stent is in an expanded state within the blood vessel and each slit is in a closed position, pressures acting on the portions of the membrane on opposing sides of each slit urge the portions of the membrane towards each other so as to provide a substantially tight closure of the slit.

14. The device as claimed in claim 8, wherein the membrane is a sleeve configured to receive the stent.

15. The device as claimed in claim 8, wherein the membrane is coated on the peripheral surface of the stent.

* * * * *